US012336839B2

(12) United States Patent
Udupa et al.

(10) Patent No.: US 12,336,839 B2
(45) Date of Patent: Jun. 24, 2025

(54) QUANTITATIVE DYNAMIC MRI (QDMRI) ANALYSIS AND VIRTUAL GROWING CHILD (VGC) SYSTEMS AND METHODS FOR TREATING RESPIRATORY ANOMALIES

(71) Applicants: The Children's Hospital of Philadelphia, Philadelphia, PA (US); The Trustees of the University of Pennsylvania, Philadelphia, PA (US)

(72) Inventors: Jayaram K. Udupa, Philadelphia, PA (US); Yubing Tong, Springfield, PA (US); Drew A. Torigian, Philadelphia, PA (US); You Hao, Philadelphia, PA (US); Changjian Sun, Philadelphia, PA (US); Joseph M. McDonough, Ambler, PA (US); Patrick J. Cahill, Merion Station, PA (US)

(73) Assignee: The Children's Hospital of Philadelphia, Philadelphia, PA (US)

(*) Notice: Subject to any disclaimer, the term of this patent is extended or adjusted under 35 U.S.C. 154(b) by 373 days.

(21) Appl. No.: 17/794,032

(22) PCT Filed: Feb. 10, 2021

(86) PCT No.: PCT/US2021/017356
§ 371 (c)(1),
(2) Date: Jul. 20, 2022

(87) PCT Pub. No.: WO2021/163116
PCT Pub. Date: Aug. 19, 2021

(65) Prior Publication Data
US 2023/0050512 A1 Feb. 16, 2023

Related U.S. Application Data

(60) Provisional application No. 62/972,242, filed on Feb. 10, 2020.

(51) Int. Cl.
*G06K 9/00* (2022.01)
*A61B 5/00* (2006.01)
(Continued)

(52) U.S. Cl.
CPC .......... *A61B 5/4538* (2013.01); *A61B 5/4842* (2013.01); *G06T 7/0014* (2013.01);
(Continued)

(58) Field of Classification Search
CPC ..... A61B 5/4538; A61B 5/4842; A61B 5/004; A61B 5/055; A61B 6/025; A61B 6/463;
(Continued)

(56) References Cited

U.S. PATENT DOCUMENTS

| 2012/0245453 A1 | 9/2012 | Tryggestad et al. |
| 2013/0245502 A1 | 9/2013 | Lange et al. |
| 2014/0286556 A1 | 9/2014 | Fouras et al. |

OTHER PUBLICATIONS

International Preliminary Report on Patentability and Written Opinion for International Application No. PCT/US2021/017356, issued Aug. 11, 2022, 8 pages.
(Continued)

*Primary Examiner* — Duy M Dang
(74) *Attorney, Agent, or Firm* — Buchanan Ingersoll & Rooney PC

(57) ABSTRACT

A method of analyzing thoracic insufficiency syndrome (TIS) in a subject by performing quantitative dynamic magnetic resonance imaging (QdMRI) analysis. The QdMRI analysis includes performing four-dimensional (4D) image construction of a TIS subject's thoracic cavity. The 4D image includes a sequence of two dimensional (2D) images of the TIS subject's thoracic cavity over a respiratory cycle of the TIS subject. The QdMRI analysis also includes segmenting a region of interest (ROI) within the 4D image, determining TIS measurements within the ROI, comparing the TIS measurements to normal measurements determined (Continued)

from ROIs in 4D images of the thoracic cavities of normal subjects that are not afflicted by TIS, and outputting quantitative markers indicating deviation of the thoracic cavity of the TIS subject relative to the thoracic cavities of the normal subjects.

23 Claims, 19 Drawing Sheets

(51) Int. Cl.
    *G06T 7/00*     (2017.01)
    *G06T 7/11*     (2017.01)
    *G06T 7/174*     (2017.01)
    *G06T 7/20*     (2017.01)
    *G06T 7/62*     (2017.01)
    *G06T 17/00*     (2006.01)
    *G06V 10/22*     (2022.01)

(52) U.S. Cl.
    CPC ............... *G06T 7/11* (2017.01); *G06T 7/174* (2017.01); *G06T 7/20* (2013.01); *G06T 7/62* (2017.01); *G06T 17/00* (2013.01); *G06V 10/22* (2022.01); *G06T 2207/10088* (2013.01); *G06T 2207/20081* (2013.01); *G06T 2207/30048* (2013.01); *G06T 2207/30061* (2013.01); *G06T 2207/30196* (2013.01)

(58) Field of Classification Search
    CPC ......... A61B 6/486; A61B 6/5288; A61B 5/00; G01R 33/5676; G01R 33/563; G06T 7/0012; G06T 7/0014; G06T 7/11; G06T 7/174; G06T 7/20; G06T 7/62; G06T 17/00; G06T 2207/10088; G06T 2207/20081; G06T 2207/30048; G06T 2207/30061; G06T 2207/30196; G06V 10/22

See application file for complete search history.

(56) References Cited

OTHER PUBLICATIONS

International Search Report and Written Opinion issued in PCT Application No. PCT/US2021/017356 mailed Jun. 23, 2021, 10 pages.

QUANTITATIVE DYNAMIC MRI (QDMRI) ANALYSIS AND VIRTUAL GROWING CHILD (VGC) SYSTEMS AND METHODS FOR TREATING RESPIRATORY ANOMALIES

CROSS-REFERENCE TO RELATED APPLICATIONS

[2] This application is a U.S. National Phase Application of PCT International Application No. PCT/US2021/017356, filed Feb. 10, 2021, which claims priority to U.S. Provisional Patent Application No. 62/972,242, filed Feb. 10, 2020, entitled "QUANTITATIVE DYNAMIC MRI (QDMRI) ANALYSIS AND VIRTUAL GROWING CHILD (VGC) AND METHODS FOR TREATING RESPITORY ANOMALIES" the contents of which are incorporated herein by reference in their entirety.

FIELD

The subject matter disclosed herein relates to devices, systems and methods for treating respiratory anomalies.

BACKGROUND

Thoracic Insufficiency Syndrome (TIS) is a class of signs and symptoms associated with a group of serious disorders of the pediatric thorax resulting in an inability of the thorax to support respiration and/or lung growth. TIS is associated with at least 28 pediatric syndromes, with an estimated incidence of 12.4 births per 10,000 and 3,000 births annually in the US, and an estimated yearly health care cost per patient that exceeds a million dollars. Intact early pulmonary function is vital for healthy life and normal growth. In TIS, 3D deformity of the thoracic components anatomically and functionally reduces the volume available for ventilation.

Over the past 100 years, many orthopedic procedures have been developed for correcting spine deformity, including spinal fusion, to reduce its adverse effects upon both spine growth and lung function over time. Growth sparing/promoting methods, such as growing rods and vertical expandable prosthetic titanium rib (VEPTR) that stabilize/correct these deformities with less adverse impact on growth, have also been developed. However, none of these methods have ever been assessed by a robust dynamic quantitative metric incorporating regional thoracic function.

SUMMARY

A method of analyzing thoracic insufficiency syndrome (TIS) in a subject. The method comprising the steps of performing, by a processor, quantitative dynamic magnetic resonance imaging (QdMRI) analysis by performing, by a processor, four-dimensional (4D) image construction of a TIS subject's thoracic cavity, the 4D image includes a sequence of two dimensional (2D) images of the TIS subject's thoracic cavity over a respiratory cycle of the TIS subject, segmenting, by the processor, a region of interest (ROI) within the 4D image, determining, by the processor, TIS measurements within the ROI, comparing, by the processor, the TIS measurements to normal measurements determined from ROIs in 4D images of the thoracic cavities of normal subjects that are not afflicted by TIS, and outputting, by the processor, quantitative markers indicating deviation of the thoracic cavity of the TIS subject relative to the thoracic cavities of the normal subjects.

A method for creating a virtual growing child (VGC) database of anatomic models for use in analyzing thoracic insufficiency syndrome (TIS) in a subject. The method comprising the steps of creating, by a processor, VGC database of anatomic models by performing, by a processor, four-dimensional (4D) image constructions of the thoracic cavities of normal subjects that are not afflicted by TIS, the 4D images each include a sequence of two dimensional (2D) images of the normal subject's thoracic cavity over a respiratory cycle of the normal subject, segmenting, by the processor, a region of interest (ROI) within each of the 4D images, determining, by the processor, normal measurements within each of ROI, generating, by the processor, based on the normal measurements, a group-wise anatomic model representing an average thoracic cavity of the normal subjects, generating, by the processor, based on the normal measurements, a group-wise dynamic model representing an average respiratory cycle of the thoracic cavity of the normal subjects, generating, by the processor, based on the normal measurements, a growth model representing growth of the thoracic cavity of the normal subjects over time, categorizing, by the processor, measurements from the group-wise anatomic model, the group-wise dynamic model and the growth model, and outputting the categorized measurements for comparison to TIS measurements of a TIS subject.

A method for analyzing heart abnormalities in a subject. The method comprising the steps of performing, by a processor, quantitative dynamic magnetic resonance imaging (QdMRI) analysis by performing, by a processor, four-dimensional (4D) image construction of a subject's heart, the 4D image includes a sequence of two dimensional (2D) images of the subject's heart over a cardiac cycle of the subject, segmenting, by the processor, a region of interest (ROI) within the 4D image, determining, by the processor, heart measurements within the ROI, comparing, by the processor, the heart measurements to normal measurements determined from ROIs in 4D images of the heart of normal subjects that are not afflicted by heart abnormalities, and outputting, by the processor, quantitative markers indicating deviation of the heart of the subject relative to the heart of the normal subjects.

A method for creating a virtual growing child (VGC) database of anatomic models for use in analyzing heart abnormalities in a subject. The method comprising the steps of performing, by a processor, VGC analysis by performing, by a processor, four-dimensional (4D) image constructions of the hearts of normal subjects that are not afflicted by heart abnormalities, the 4D images each include a sequence of 2D dimensional (2D) images of the normal subject's heart over a cardiac cycle of the normal subject, segmenting, by the processor, a region of interest (ROI) within each of the 4D images, determining, by the processor, normal measurements within each of ROI, generating, by the processor, based on the normal measurements, a group-wise anatomic model representing an average heart of the normal subjects, generating, by the processor, based on the normal measurements, a group-wise dynamic model representing an average heart of the normal subjects, generating, by the processor, based on the normal measurements, a growth model representing growth of the heart of the normal subjects over time, categorizing, by the processor, measurements from the group-wise anatomic model, the group-wise dynamic model and the growth model, and outputting the categorized measurements for comparison to heart measurements of a heart subject with heart abnormalities.

A method of analyzing a clinical condition that affects a thoracic respiratory function in an afflicted subject. The method comprising the steps of performing, by a processor, quantitative dynamic magnetic resonance imaging (QdMRI) analysis by performing, by a processor, four-dimensional (4D) image construction of the afflicted subject's thoracic cavity, the 4D image includes a sequence of two dimensional (2D) images of the afflicted subject's thoracic cavity over a respiratory cycle of the afflicted subject, segmenting, by the processor, a region of interest (ROI) within the 4D image, determining, by the processor, afflicted measurements within the ROI, comparing, by the processor, the afflicted measurements to normal measurements determined from ROIs in 4D images of the thoracic cavities of normal subjects that are not afflicted, and outputting, by the processor, quantitative markers indicating thoracic respiratory function deviation of the afflicted subject relative to the respiratory function of the normal subjects.

A method of performing four-dimensional (4D) image construction of an anatomical feature of a subject. The method comprising the steps of estimating, by a processor, a motion vector field for the anatomical feature from successive two-dimensional (2D) images over a time period, and outputting repetitive cycles, filtering out, by the processor, abnormal cycles from the repetitive cycles, and assembling, by the processor, canonical cycles from the filtered repetitive cycles and assembling the canonical cycles into the 4D image.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and circuitry have been described at a relatively high-level, without detail, in order to avoid unnecessarily obscuring aspects of the present teachings.

Introduction

Figure 1A:
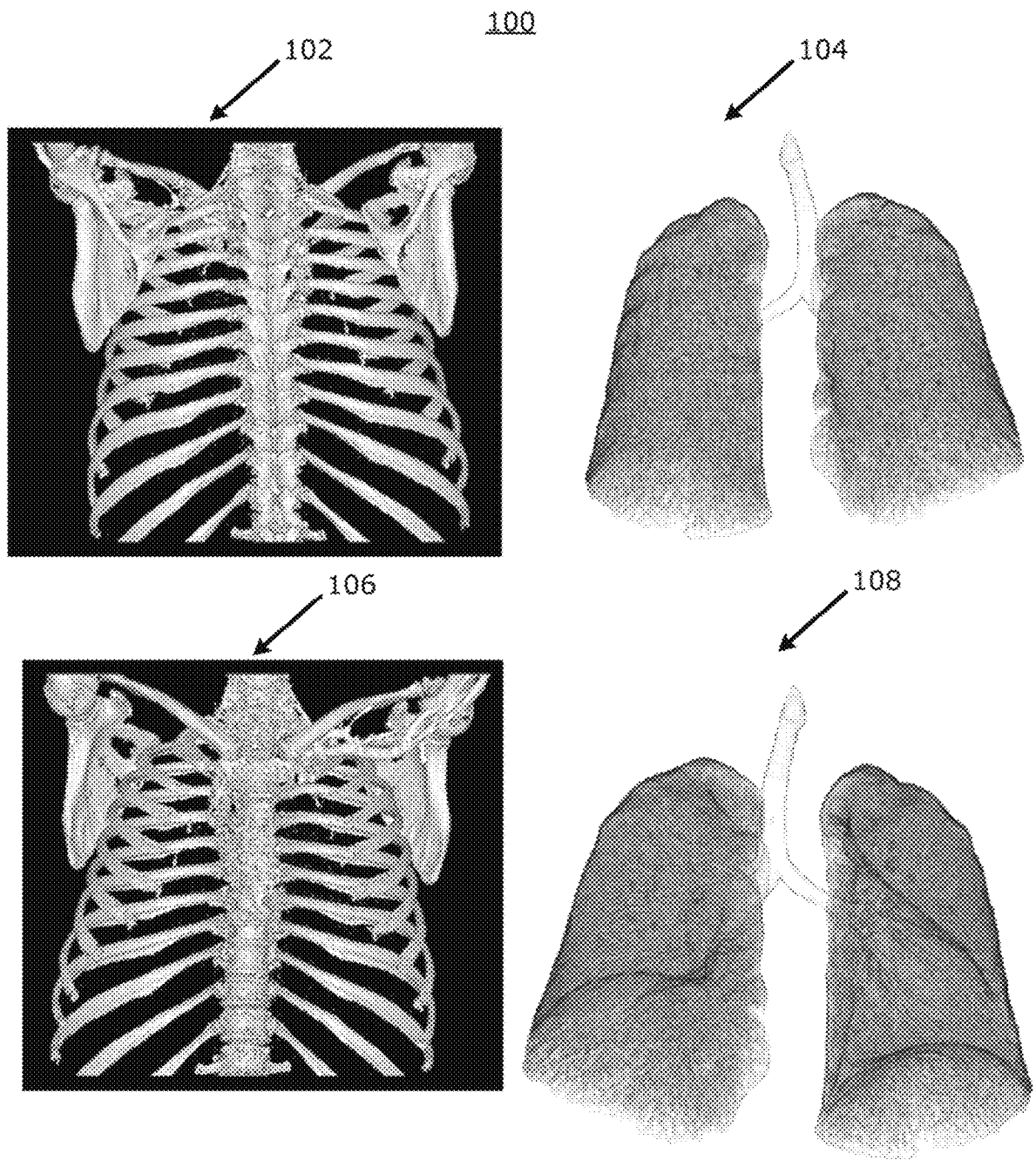
FIG. 1A is a posterior and anterior view of a thoracic cavity and lungs of a normal subject, according to an aspect of the disclosure.
Figure 1B:
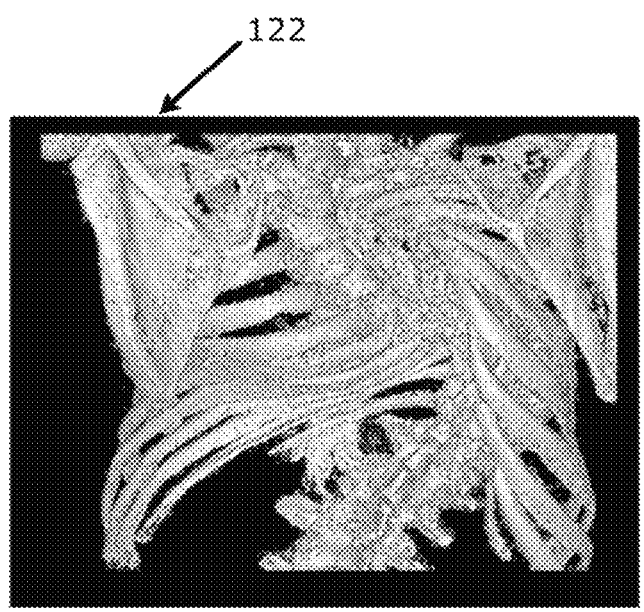
FIG. 1B is a posterior and anterior view of a thoracic cavity and lungs of a thoracic insufficiency syndrome (TIS) subject, according to an aspect of the disclosure.
Figure 1B:
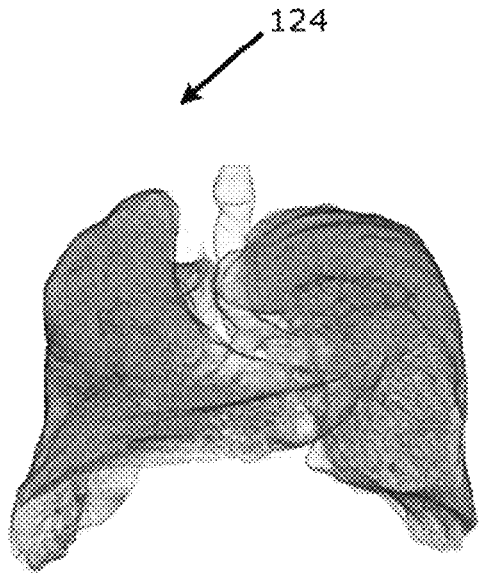
Figure 1B:
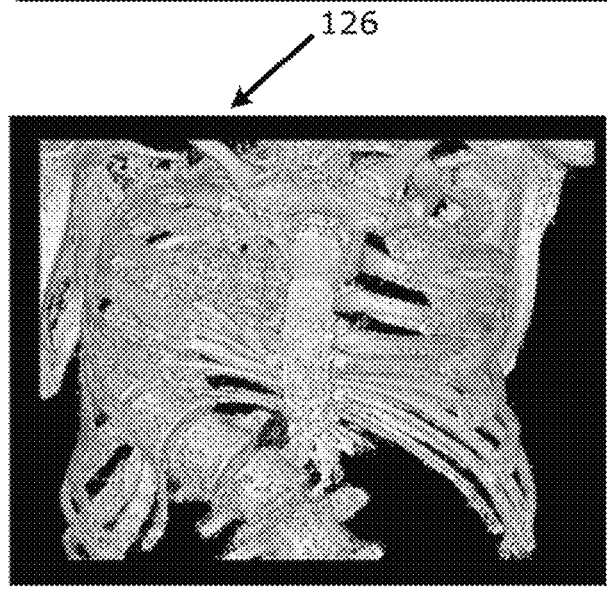
Figure 1B:
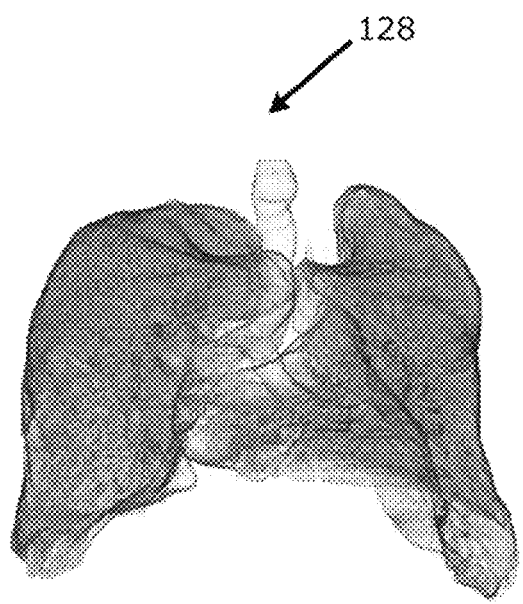

FIG. 1A shows a posterior view and anterior view of a thoracic cavity of a normal (i.e. non-TIS) subject 100. In posterior/anterior views 102 and 106, it is shown that the rib cage of normal subject 100 has formed properly with growth, thereby providing adequate internal volume for proper lung growth as shown in posterior/anterior normal lung views 104 and 108. In contrast, FIG. 1B shows a posterior view and anterior view of a thoracic cavity of a TIS subject 120. In posterior/anterior views 122 and 126 it is shown that the rib cage of TIS subject 120 has formed improperly due to scoliosis. This improper growth results in inadequate internal volume for proper lung growth (i.e. lung growth is restricted). The inadequate lung growth of TIS subject 120 is shown in posterior/anterior abnormal lung views 124 and 128.

Pediatric specialists dealing with TIS subjects are faced with serious challenges. Specifically, these challenges include, but are not limited to: a) the interplay among thoracic structures and its influence on thoracic function and growth are currently not understood, b) prime treatment outcome measure for TIS has remained a 60-year-old metric, the radiographic angle (called Cobb angle) of the spine. However, there is no correlation between Cobb angle and lung vital capacity before surgery or between the changes in these entities after surgery, c) a database of functional metrics describing regional dynamics and growth of the thoracic structures of the normal pediatric population does not exist, and d) systematic innovations in growth-modulating surgical procedures are therefore difficult to achieve.

To overcome the above challenges, the present application proposes two innovative technologies for the assessment of TIS, the prediction of TIS progression and the recommendation for surgical procedures to treat TIS. The first of these technologies is a quantitative dynamic magnetic resonance imaging (QdMRI) analysis for developing thoracic cavity measurements from dMRI images of a TIS subject. The second of these technologies is a Virtual Growing Child (VGC) smart database which uses an ensemble of dMRI images of a group of normal (e.g. non-TIS) subjects to determine thoracic cavity measurements, and develop functional models depicting the dynamics and growth of the thoracic components derived from normal pediatric subjects over the entire pediatric age spectrum.

Both the QdMRI analysis and the VGC smart database are combined to form an overall QdMRI-VGC system that is used to assess TIS subjects, predict TIS progression in the subjects over time, and recommend surgical procedures to treat the TIS subject. There are several elements in the QdMRI-VGC system. These elements are described in detail below.

QDMRI-VGC System

Figure 2A:
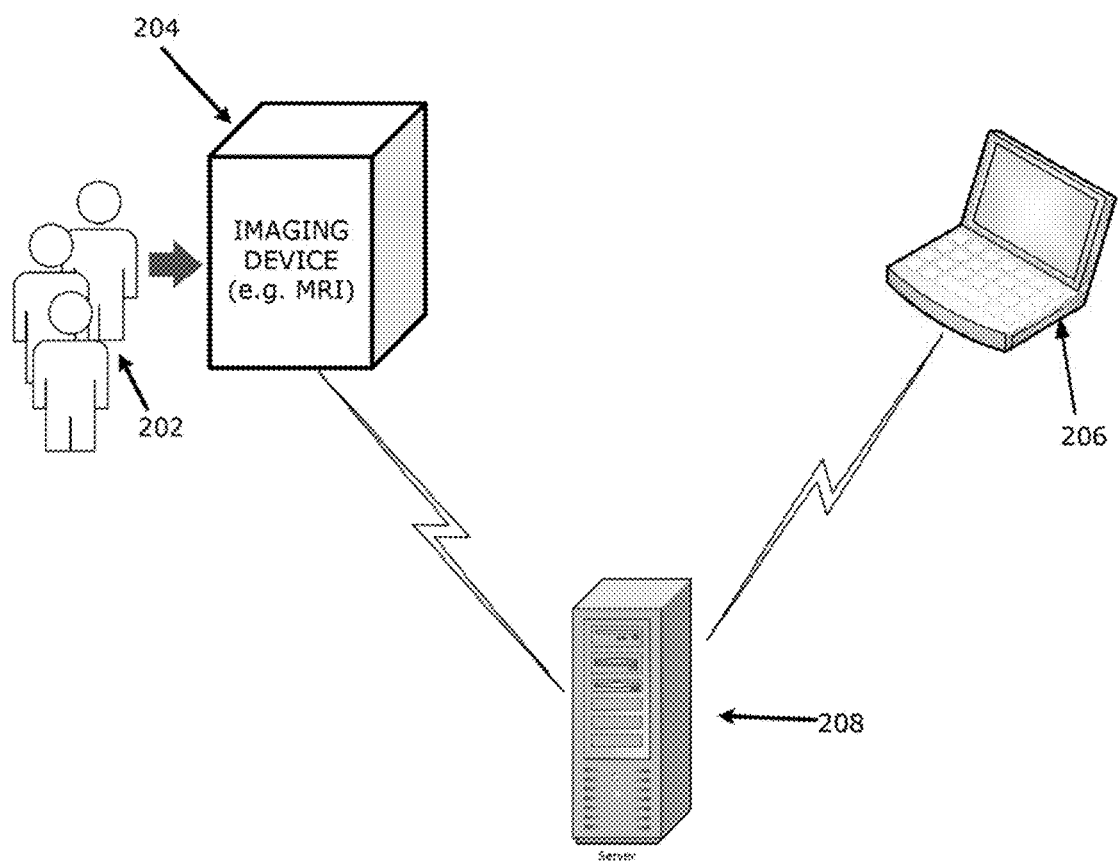
FIG. 2A is a QdMRI-VGC system diagram, according to an aspect of the disclosure.

FIG. 2A shows a view of the QdMRI-VGC system diagram. In this example, the QdMRI-VGC system includes an MRI imaging device 204 and a computer 206 which are in communication with server 208. During operation, subjects 202 (e.g. TIS subjects and normal subjects) are individually scanned by MRI imaging device to capture dMRI images of their thoracic cavities. The dMRI images of TIS and normal subjects 202 are stored in server 208. Although the QdMRI-VGC system/methods described through the application are performed on MRI images, the systems/methods may also be used on other types of images such as computerized tomography (CT) scan images.

Figure 2B:
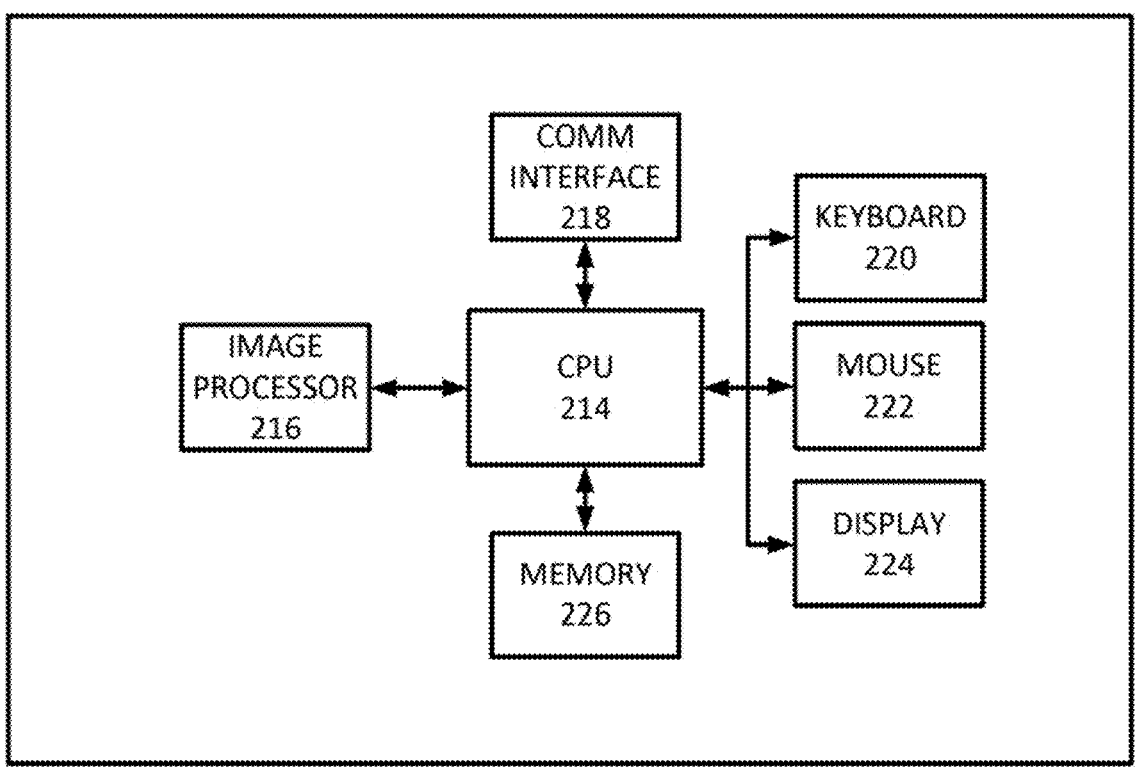
FIG. 2B is a block diagram of a computer and/or server of the QdMRI-VGC system, according to an aspect of the disclosure.

Details of computer 206 of the QdMRI-VGC system in FIG. 2A are shown in FIG. 2B. Specifically, computer 206 includes central processing unit 214, image processor 216 including Graphical Processing Units, communication interface 218 (e.g. WiFi, Bluetooth, etc.), memory device 226 and user input/output devices such as keyboard 220, mouse 222, and display 224. Although computer 206 is shown in FIG. 2A as a laptop computer, computer 206 may be a desktop computer, smartphone, tablet computer, and any other equivalent for executing methods of the QdMRI-VGC system. Server 208 may also have hardware components similar to those shown in FIG. 2B.

During operation, computer 206 retrieves the dMRI images from server 208 and executes the methods of the QdMRI-VGC system. For example, computer 206 uses communication interface 218 to communicate with server 208 and retrieve the dMRI images. These images are then processed by image processor 216 to perform the assessment of a TIS subject, the prediction of TIS progression in the TIS subject, and the recommendation for surgical procedures to treat the TIS subject.

Figure 3:
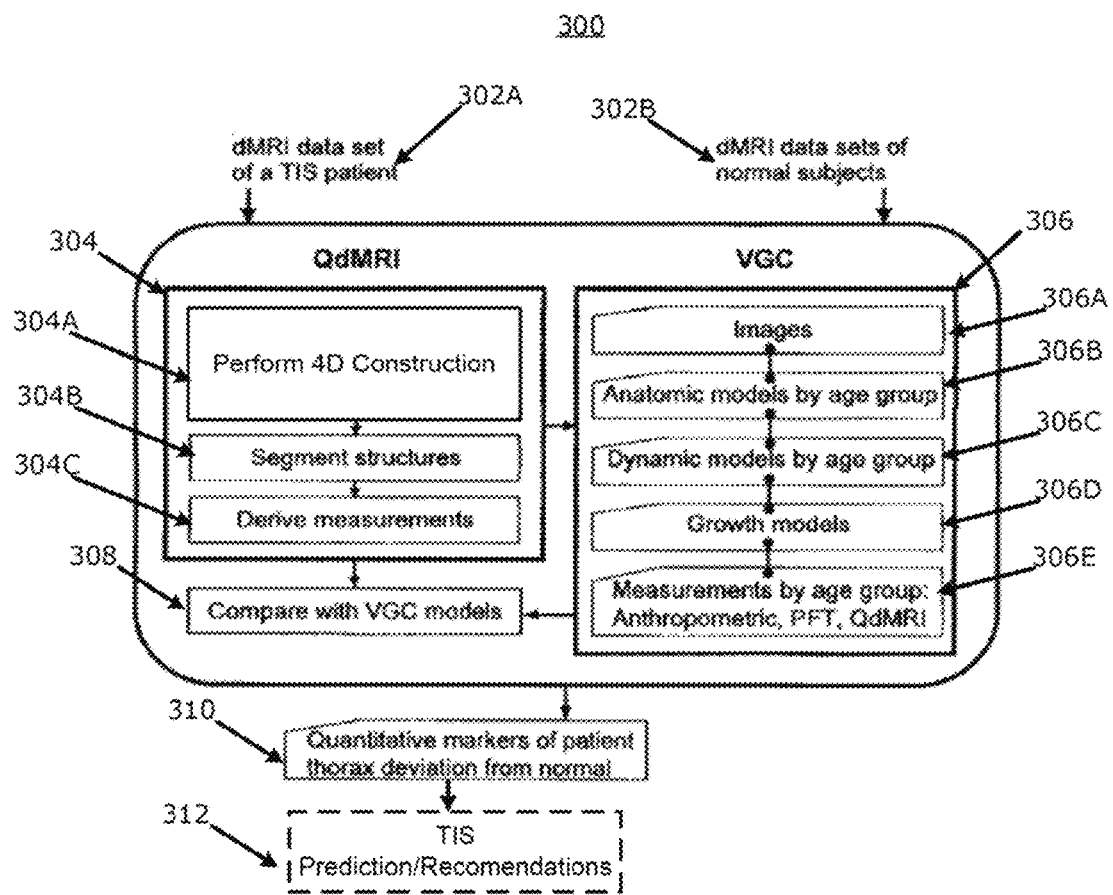
FIG. 3 is a QdMRI-VGC flowchart showing methods of the QdMRI-VGC system, according to an aspect of the disclosure.

FIG. 3 is a QdMRI-VGC flowchart 300 showing the two major components (subsystems) of the QdMRI-VGC system. These include QdMRI methodology 304 and the VGC subsystem 306. The QdMRI methodology 304 includes three key steps 304A-304C, while the VGC subsystem 306 is a smart knowledgebase created by applying the QdMRI methodology to dMRI scans of normal subjects. The resulting VGC ensemble (knowledge base) includes (see boxes 306A-306E) the acquired dMRI images, thoracic structures segmented in these dMRI scans, and various models such as anatomic, dynamic, and growth models created for each age group in the normal subject population. The VGC subsystem also contains pulmonary function testing (PFT) measurements and anthropometric measurements taken from normal subjects, and a host of other measurements derived from the QdMRI methodology that describe the morphological, architectural, dynamic, growth-related, and tissue-related information pertaining to the normal population organized by age group. Note that all five boxes 306A-306E shown under the VGC subsystem are catalogs housing the different components of the smart knowledge base. These catalogs are computed by computer 206 and/or server 208. Further details of the QdMRI-VGC system are found in the document beginning with "Specific Aims" filed concurrently herewith as Document5, which is incorporated by reference herein in its entirety.

OdMRI

The QdMRI methodology 304, as shown in FIG. 3, includes three primary steps 304A-304C that may be performed by computer 206 to obtain results which are then stored in server 208.

Figure 4A:
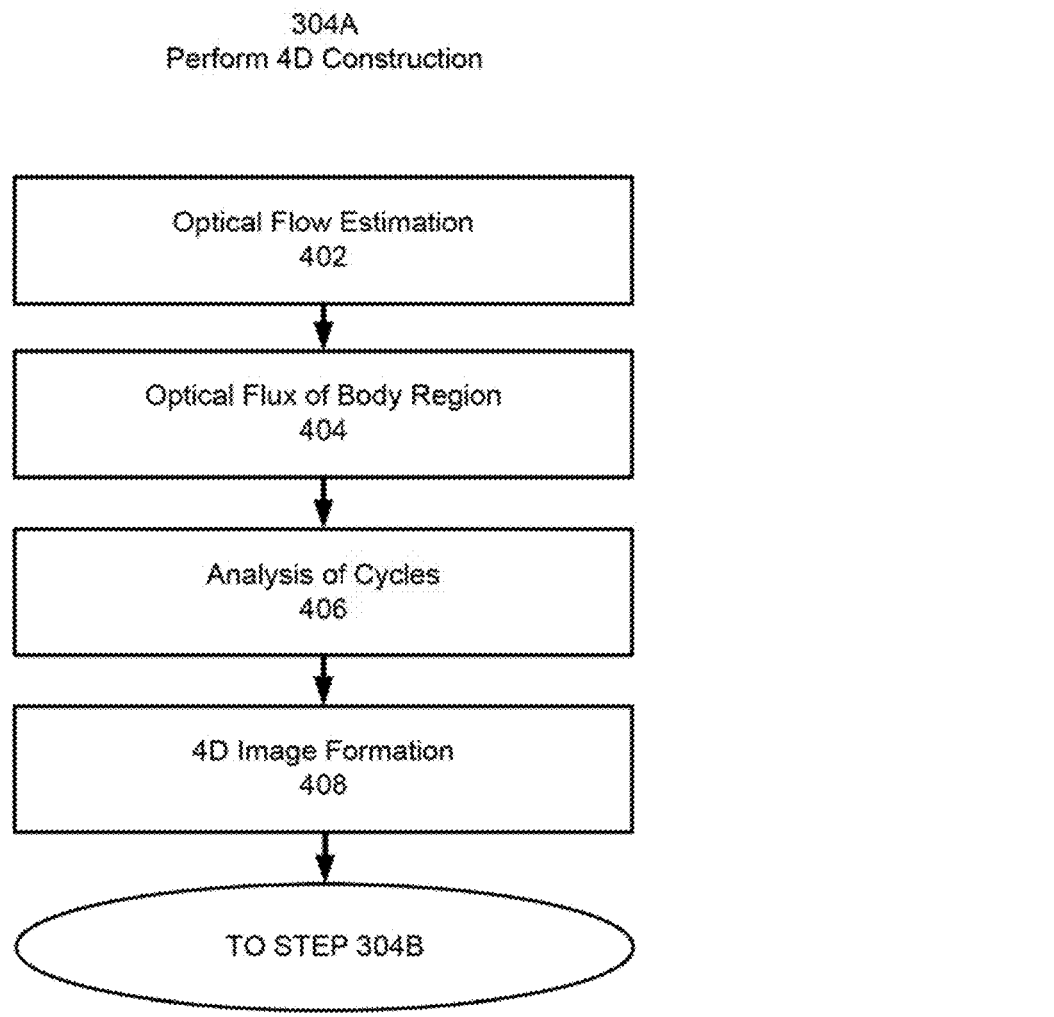
FIG. 4A is a flowchart of the 4D construction step in the QdMRI-VGC flowchart, according to an aspect of the disclosure.

The first primary step of the QdMRI methodology, as shown in FIG. 4A is a 4D construction step 304A. The dMRI free-breathing acquisition of a patient (e.g. TIS subject) typically yields about 3000 slices. These slices constitute a somewhat random sampling of the breathing thorax in space and time over several respiratory cycles. The 4D construction step selects a subset of slices (e.g. roughly 300 slices) from the 3000 slices to constitute a consistent breathing thorax over exactly one cycle. The overall 4D image construction, includes three main computations: respiratory signal extraction, respiratory cycle analysis, and 4D image formation.

In the first step, in order to extract the respiratory signal in the first step, optical flow estimation 402 is performed, and optical flux information 404 is derived. Optical flux information can be regarded as a respiratory surrogate, which is computed from the time-series of slices associated with each sagittal location of the thoracic cavity to extract all potential cycles. The optical flow generates a vector field which is a mapping from the discrete body region to the vectors in the 3D space corresponding to a time instance. In other words, for every pixel identified in the dMRI image slice, the system assigns a vector which indicates the velocity vector at that time. Since optical flow is estimated based on an identified discrete body region, this reduces the impact of background noise from outside the body region influencing analysis within the body region. This idea is beneficial for capturing the motion of lungs and hemi-diaphragms during the respiratory cycle accurately.

Flux, as described above, is a property associated with a 3D region in a vector field. It represents the net "outgoingness" for that region. One typical application of flux is in electric fields. In this application, however, the system has the vector field generated by the optical flow to capture the motion of the tissues within the body region. During inspiration, the chest wall and diaphragm move outward with respect to the lung tissues, which will be reflected in the outward direction of the vectors (i.e. from the electric field analogy, this situation is as if there is positive electric charge inside the chest and negative charge outside). Toward the end of inspiration, this outgoingness gradually decreases and reverses during inspiration at which point the vectors change direction to orient generally inwards corresponding to the inward motion of the chest wall and diaphragm (i.e. analogously, the interior positive charge gets gradually depleted toward the end of inspiration, with a reversal of charge to negative inside and positive outside during exhalation).

The method to derive flux from the vector field is through the concept of divergence, (or derivative) of the vector field. Divergence at a point (pixel) p is a local measure of outgoingness at p. In other words, it denotes the amount of outward flux locally within an infinitesimal volume (area) around p.

In step 406, a full analysis of these cycles is conducted at each location based on the flux data to extract all near-normal cycles. Step 406 also includes three sub-steps.

In the first sub-step, the system identifies end-inspiration (EI) and end-expiration (EE) time points in order to partition the data into respiratory cycles (i.e. EI and EE are auto-labeled based on flux information). If all respiratory cycles are near-normal, the system detects EI and EE points easily depending on the zero-crossings of the flux curve. However, abnormal patterns may exist due to shallow-breathing or breath holding patterns. Thus, to detect EI and EE points more accurately, the system first finds all peaks on the flux curve and then filters out peaks with values close to zero. Then, following the time sequence, the system finds the last time point (slice) with positive flux after each peak as an EI point and the first slice with negative flux before each peak as an EE point.

In the second sub-step, the system derives features from the extracted cycles. Among others, these features include flux volume during inspiration and expiration, number of peaks and valleys, time distance between peaks, and breath holding intervals.

In the third sub-step, the system filters cycles by sifting through the set of all cycles to output just the set of normal cycles and their associated set of image sequences. To achieve this, the system devises a loss function which assigns a cost value to each cycle, with a higher cost indicating the degree of deviation from normality.

In step 408, the system aligns all near-normal cycles to one canonical respiration model and proposes one cycle for each sagittal location independently. These proposed cycles are then combined from all sagittal locations to form the final 4D image volume. Since slices are acquired under free breathing conditions, the number of and the actual respiratory phases of sampled time points in cycles are different. However, once the system performs a cosine fit to the cycles, each separately, the system knows within the fit cosine model the exact phase of each time instance in the two cycles. The basis for this idea is the use of flux as a surrogate for respiratory function. The flux value for each time slice can be regarded as the moving velocity of the slice. For each cycle, the system estimates the moved distance from velocity for each time slice by accumulation, which can be regarded as the tidal volume (change in volume of a structure from EI to EE) signal of the slice in the cycle. For all cycles, the system normalizes the position signal. Following this procedure, the system aligns all time slices of the cycles into the cosine model. Further details of the QdMRI steps 402-408 are found in Hao, et al., "*OFx: A method of 4D image construction from free-breathing non-gated MRI slice acquisitions of the thorax via optical flux*", which is filed concurrently herewith as Document1, and is incorporated by reference herein in its entirety.

Figure 4B:
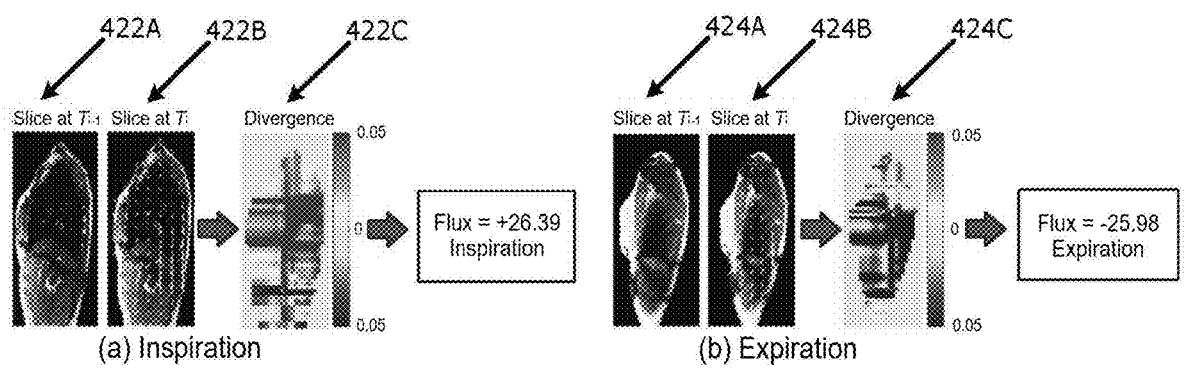
FIG. 4B is an example of optical flow from the 4D construction step, according to an aspect of the disclosure.

FIG. 4B is an example of optical flow 420 from the 4D construction step 304A. As shown, for inspiration, the optical flow vectors estimated from slices 422A/422B have divergence 422C which results in a positive flux. In contrast, for expiration, the optical flow vectors estimated from slices 424A/424B have divergence 424C which results in a negative flux.

Figure 4C:
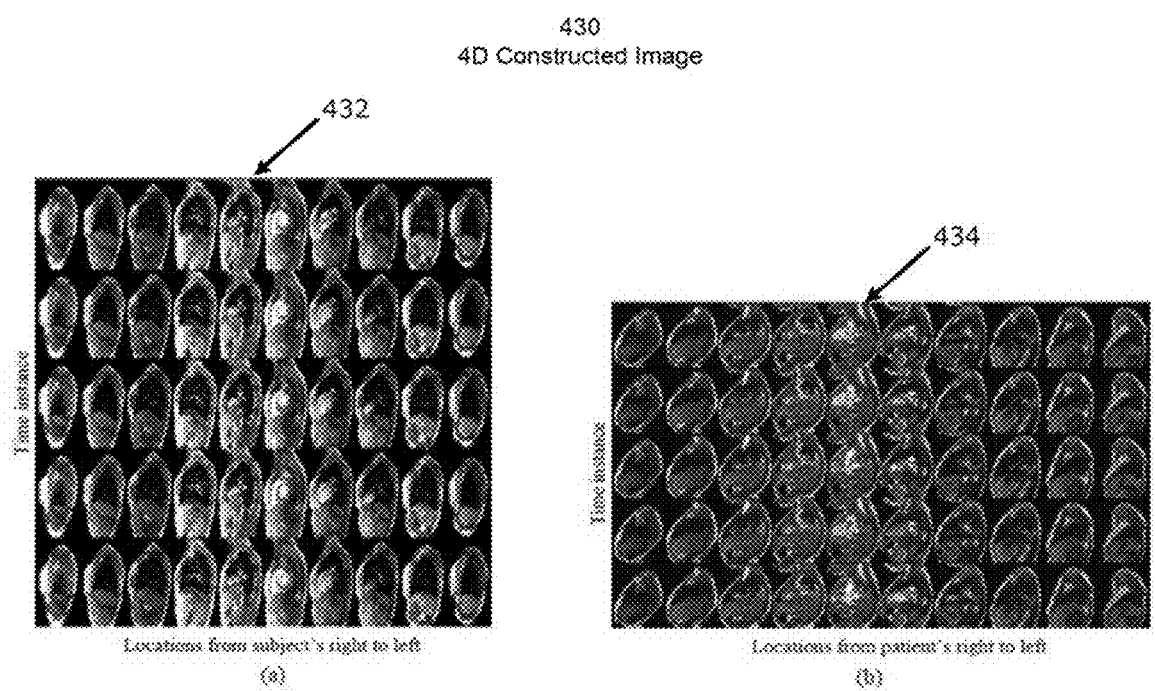
FIG. 4C is an example of a 4D constructed image produced by the 4D construction step, according to an aspect of the disclosure.

As described with reference to FIG. 4A, 4D images are constructed. An example of 4D constructed images 430 is shown in FIG. 4C. 4D images 432 are slices from a normal subject, whereas images 434 are slices from a TIS subject.

Figure 5A:
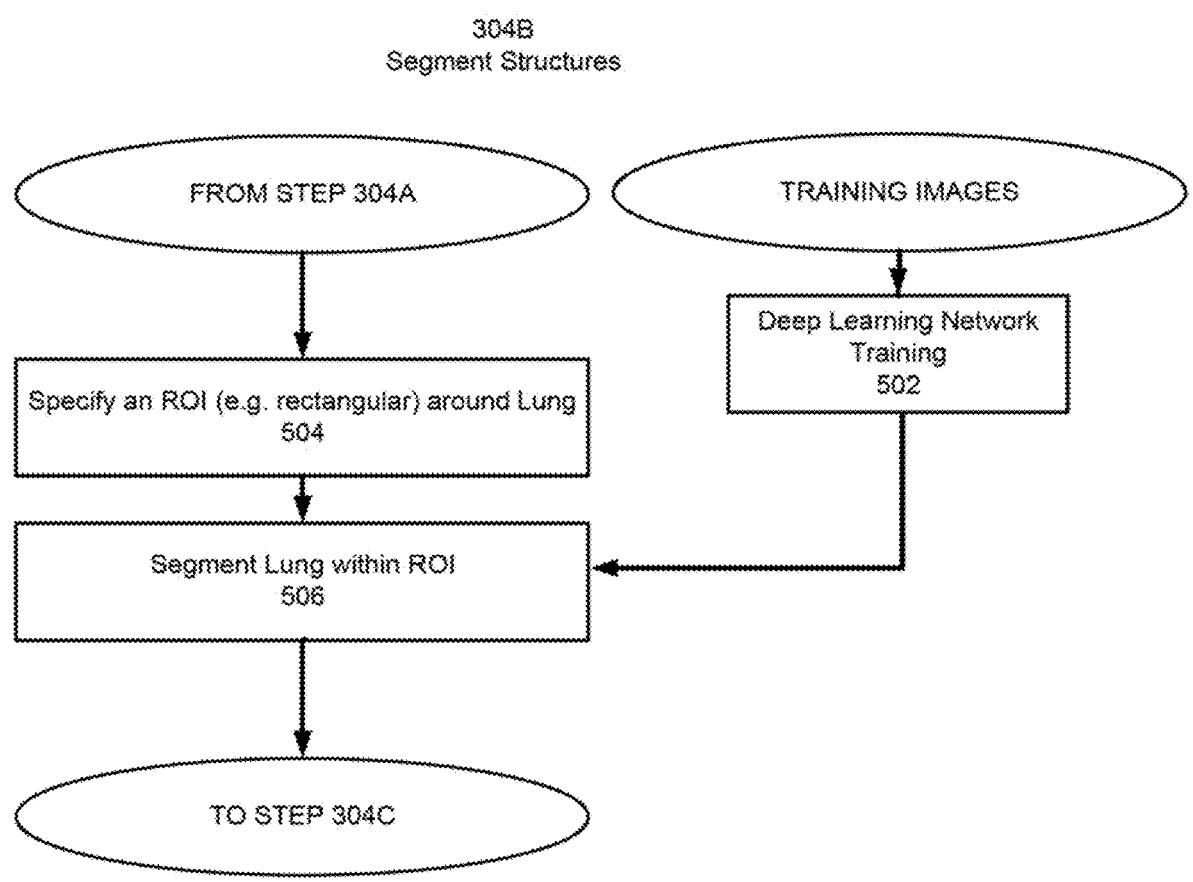
FIG. 5A is a flowchart of the segmentation step in the QdMRI-VGC flowchart, according to an aspect of the disclosure.

After 4D construction is complete, the second primary step of the QdMRI methodology segments the lungs from the background in the image. Left and right lungs are segmented separately in each of EI and EE time points of the 4D image. FIG. 5A is a flowchart of the segmentation step 304B which implements a deep learning (DL) based method. A DL (e.g. 2D U-Net DL) architecture is employed and adapted to this TIS application. This approach includes a training step 502 where the DL network is trained with many examples of dMRI image slices and true segmentations of the lungs. Subsequently this trained network is employed to perform segmentations in step 506 in a slice-by-slice manner for a ROI specified in step 504 or any given 3D image corresponding to the EE or EI time point of the 4D constructed image. Note that DL training is performed only once, and the same trained network is then used repeatedly to segment every patient data set. FIG. 5C is an illustration of the architecture of the U-Net showing its parameters in different layers. Further details of the general operation of U-Net DL is found in Ronneberger, et al., "*U-Net: Convolutional Networks for Biomedical Image Segmentation*", Computer Science Department and BIOSS Centre for Biological Signalling Studies, University of Freiburg, Germany, arXiv:1505.04597v1 [cs·CV] 18 May 2015, which is filed concurrently herewith as Document7, and which is incorporated by reference herein in its entirety.

After training the DL network, the segmentation process includes first specifying a rectangular region of interest (ROI) (see FIG. 5B) around the lung region on the sagittal slice passing through the middle of the ipsilateral hemi-diaphragm at EI time point of the 4D image. Then, the ROI is propagated to all other slices automatically. Segmentation is then performed automatically on all 2D slices within the ROI.

Figure 5B:
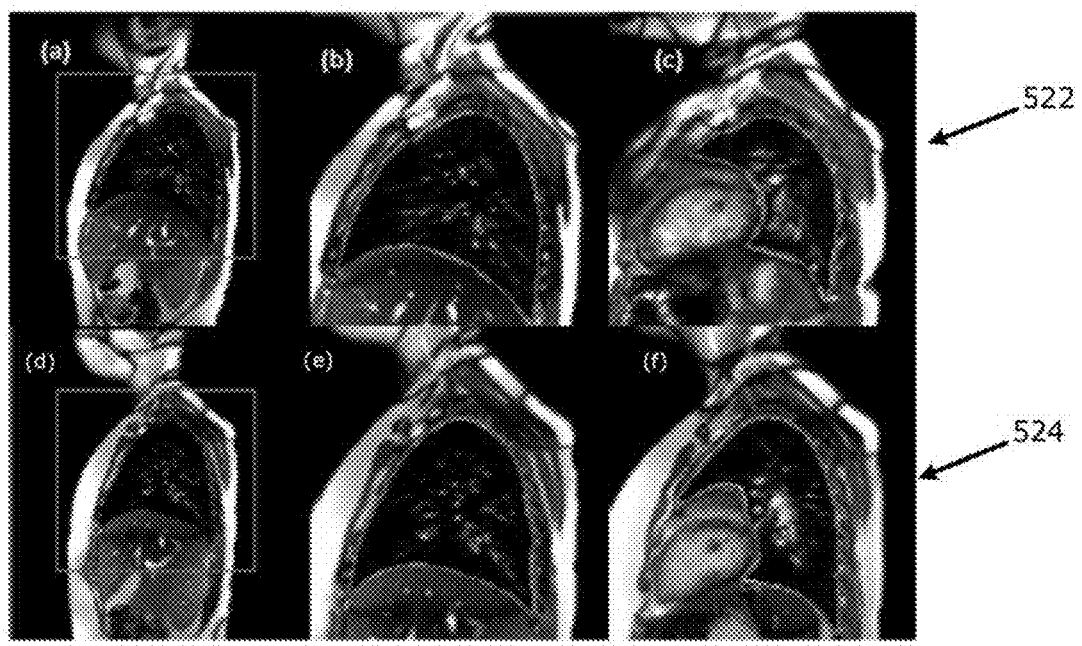
FIG. 5B is an example of segmented images produced by the segmentation step, according to an aspect of the disclosure.
Figure 5C:
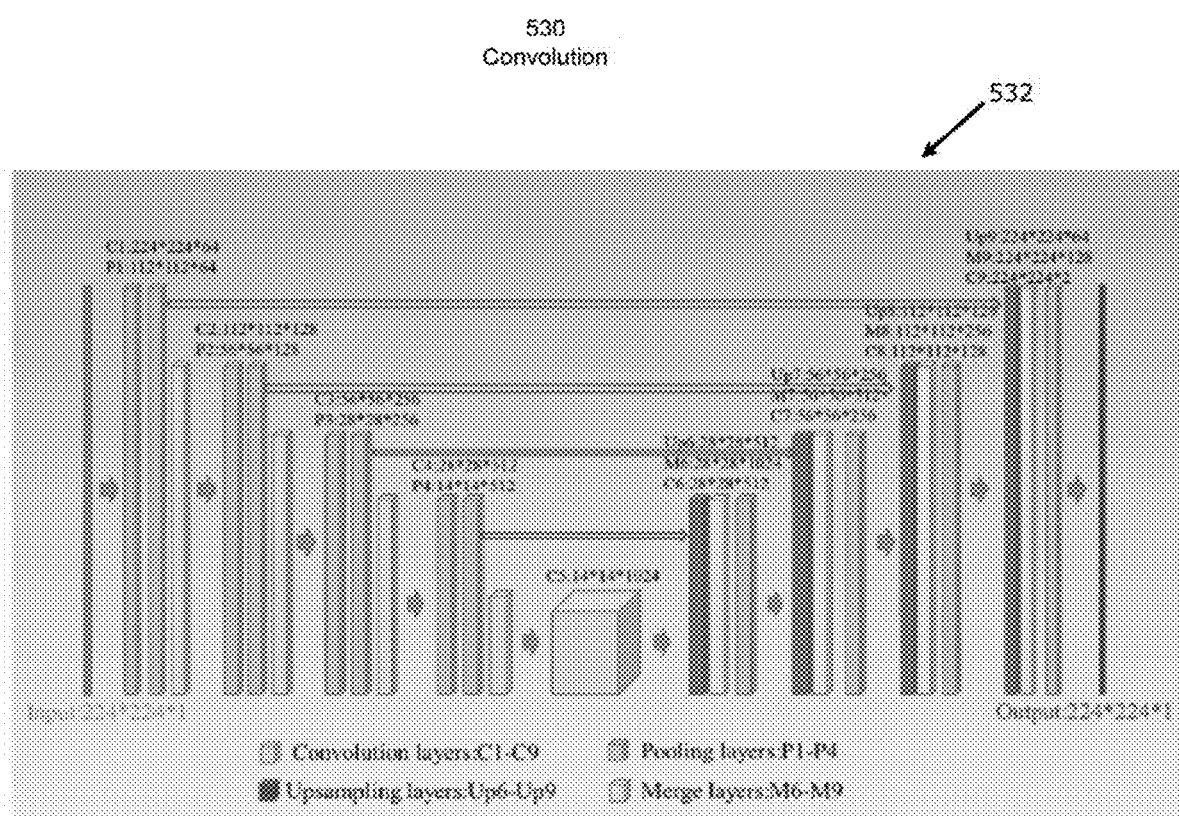
FIG. 5C is an architectural diagram of the U-Net showing its parameters.

FIG. 5B is an example 520 of segmented images produced by the segmentation step. Top row 522 shows a dMRI slice from a normal male subject with a rectangular ROI placed around the right lung (image (a)); its manual true segmentation of the lung boundary overlapped with the DL segmentation of the boundary (image (b)); and a dMRI slice through the left lung of the same subject together with overlapping true and DL segmentations of its boundary (image (c)). Bottom row 524 shows similar images (d), (e) and (f) for a normal female subject.

Figure 6:
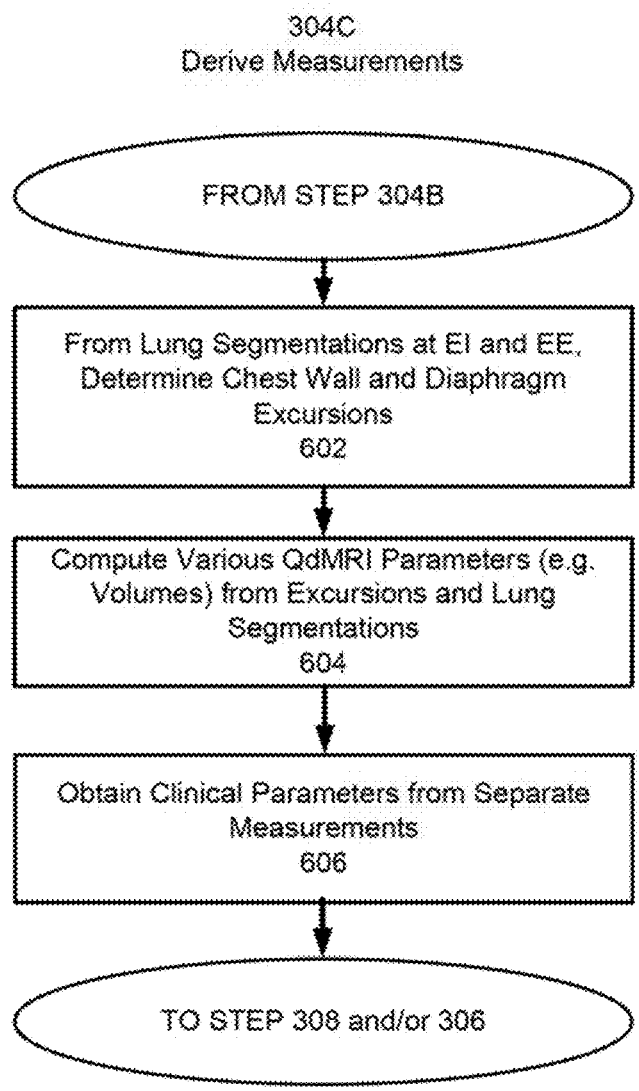
FIG. 6 is a flowchart of the measurements step in the QdMRI-VGC flowchart, according to an aspect of the disclosure.

After segmentation is performed, the third primary step of the QdMRI methodology derives measurements of the segmented lung images in step 304C. FIG. 6 is a flowchart of the measurements step 304C. In step 602, the system obtains left and right chest wall and hemi-diaphragm excursion regions from each 4D dMRI data set. These excursion regions are obtained from separate segmentations of the left and right lungs at EI and EE, by subtracting segmentations, and performing morphological operations and connected component labeling.

From the excursion regions and separate left and right lung segmentations, various QdMRI parameters such as tidal volumes and lung volumes are obtained in step 604. The tidal volume parameters obtained include but are not limited to: (bilateral) lung tidal volume, left lung tidal volume, right lung tidal volume, left chest wall tidal volume, right chest wall tidal volume, left hemi-diaphragm tidal volume, and right hemi-diaphragm tidal volume. The four lung volume parameters are left and right lung volume at EI and left and right lung volume at EE.

In step 606, the system also gathers clinical measurements that include but are not limited to: forced vital capacity and total lung capacity from pulmonary function testing, Cobb angle of spinal curves from anteroposterior radiographs, and other parameters of resting breathing rate, assisted ventilation rating, and left/right available lung space. Further general details of deriving measurements are found in Tong et al, "*Quantitative dynamic MRI (QdMRI) volumetric analysis of pediatric patients with thoracic insufficiency syndrome*", SPIE Medical Imaging Conference, Houston, TX (2018) and Tong, et al., "*Quantitative Dynamic Thoracic MRI: Application to Thoracic Insufficiency Syndrome in Pediatric Patients*", Radiology 292:206-213 (2019), which are filed concurrently herewith as Document2 and Document3, respectively, and which are both incorporated by reference herein in their entireties.

Figure 7:
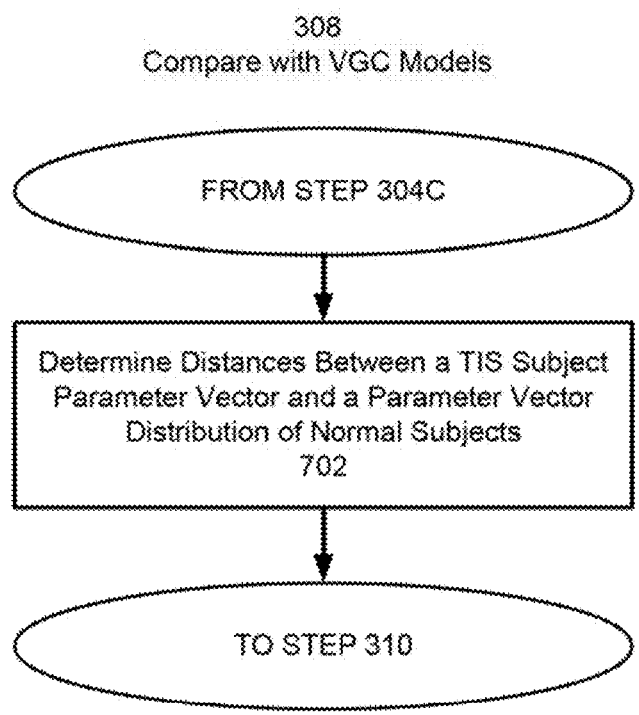
FIG. 7 is a flowchart of the comparison step in the QdMRI-VGC flowchart, according to an aspect of the disclosure.

The measurements from step 304C are then output to comparison step 308 or to VGC smart database 306. In general, comparison step 702 shown in FIG. 7 determines distances between the parameter vector of the TIS measurements of any TIS subject and distribution of the parameter vectors of measurements from normal subjects retrieved from the VGC subsystem. In order to perform such a comparison, the VGC subsystem is populated with model information. The following section discusses the details of the VGC subsystem (e.g. populating with measurements from normal subjects and generating models for comparison purposes).

VGC Subsystem

As shown in FIG. 3, the QdMRI-VGC flowchart includes VGC subsystem 306A-306E which develops models based on derived measurements received from the QdMRI subsystem and categorizes measurements for comparison. Unlike the measurements output by the QdMRI subsystem to the comparison step 308 as described above, however, the measurements received by the VGC subsystem from the QdMRI subsystem are the measurements of normal (i.e. non-TIS) subjects. Essentially, QdMRI subsystem 304 performs the same steps described above (e.g. 4D construction, segmentation, and deriving measurements) using images from normal subjects. The VGC subsystem uses these normal subject measurements to generate various models and age grouping measurements for output to comparison step 308. Each of the VGC subsystem steps is described in more detail below. It is noted that the VGC subsystem steps 306A-306E for generating the models and categorizing the measurements may be performed by computer 206, server 208, or a combination of computer 206 and server 208, and then stored in server 208.

Figure 8:
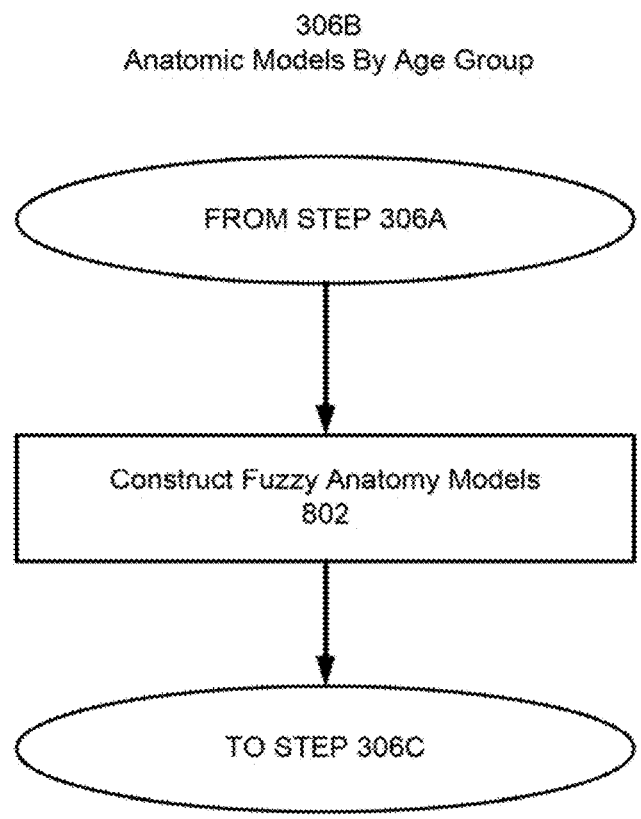
FIG. 8 is a flowchart of the anatomic model step in the QdMRI-VGC flowchart, according to an aspect of the disclosure.

FIG. 8 is a flowchart of the step 306B for generating the anatomic model for each respiratory phase for each age and gender group. Specifically, in step 802, each anatomic model built includes objects such as: skin outer boundary, the two lungs together as one object, and the two lungs as separate objects, thoracic skeleton, liver, and kidneys. A fuzzy object model is built for each object from the normal subject dMRI images and segmentations of the object. The anatomy model constructed represents an average thoraco-abdominal anatomy of the normal subjects at each point during the respiratory cycle for each age group and gender. Further general details of generating an anatomic model is found in Udupa, et al., "*Body-wide hierarchical fuzzy modeling, recognition, and delineation of anatomy in medical images*", Medical Image Analysis, 18 (2014) 752-771, which is filed concurrently herewith as Document4, and which is incorporated by reference herein in its entirety.

Figure 9:
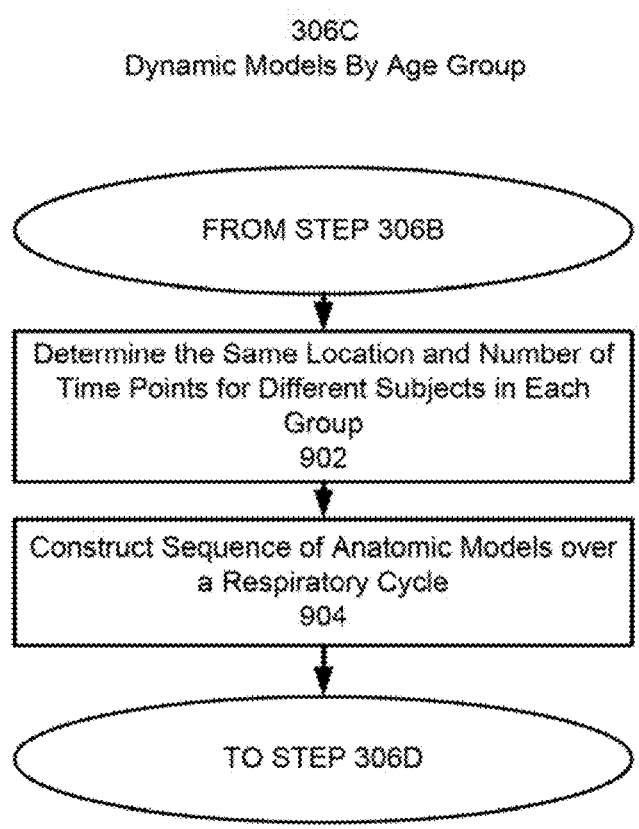
FIG. 9 is a flowchart of the dynamic model step in the QdMRI-VGC flowchart, according to an aspect of the disclosure.

FIG. 9 is a flowchart of the step 306C for generating the dynamic model for each age and gender group. Specifically, in step 902, using the method of analyzing cycles described in 406 of FIG. 4A, for all subjects in each group, the same number of time points is first determined and approximately the same time points in the cycle are sampled. The ensemble of anatomic models corresponding to these different time points of the respiratory cycle is then collected in step 904. This sequence of the anatomic models created represents an average respiratory cycle of the thoracic cavity of the normal subjects.

Figure 10:
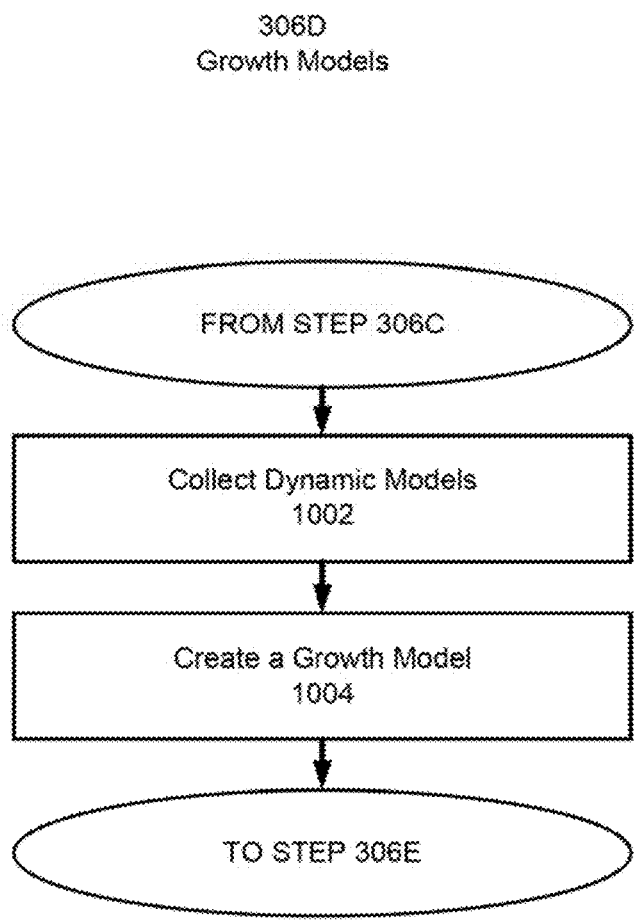
FIG. 10 is a flowchart of the growth model step in the QdMRI-VGC flowchart, according to an aspect of the disclosure.

FIG. 10 is a flowchart of the step 306D for generating the VGC growth model. In step 306C, one dynamic model is created for each group. In step 1002, the dynamic models for the different age groups are collected. In step 1004, the dynamic models are combined to create a growth model that represents growth of the thoracic cavity of the normal subjects over time. For example, for age group #n, the dynamic models corresponding to group #n-1, group #n, and group #n+1 are considered to determine how the QdMRI parameters change as an average of the change from #n-1 to #n and from #n to #n+1. To be more specific, the QdMRI parameter right hemi-diaphragmatic tidal volume is known for groups #n-1, #n, and #n+1. Therefore, the change in this parameter (e.g. a derivative of the parameter) at the instance of age corresponding to group #n can be estimated. The dynamic model associated with each age group #n together with the change in the parameters as described constitutes the growth model at age corresponding to each group #n.

Figure 11:
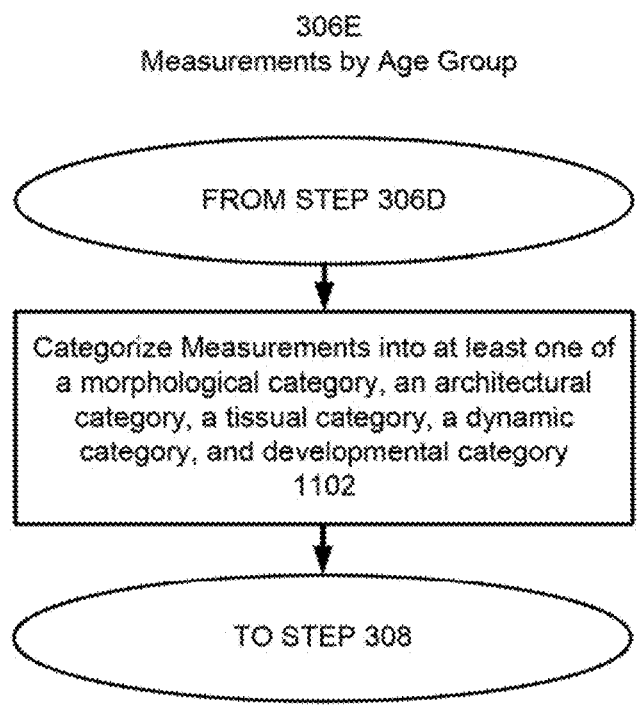
FIG. 11 is a flowchart of the measurement categorization step in the QdMRI-VGC flowchart, according to an aspect of the disclosure.

FIG. 11 is a flowchart of the step 306E for categorizing measurements. Specifically, in step 1102, the system categorizes the measurements into at least one of: a morphological category, an architectural category, a tissue category, a dynamic category, and developmental category. For example, in the morphological category, size information about objects is gathered such as the volumes. In the architectural category, relationship between objects is measured such as the distance. In the tissue category, average properties of the tissue within each object are described, such as average image intensity within the lungs or liver. In the dynamic category, measurements of how the morphological and architectural properties change with dynamics are measured. This may include, for example, how the right lung changes its volume or how the distance between right lung and the liver changes from EI to EE. In the growth category, how the morphological, tissual, architectural, and dynamic properties change from one age group to the next is described. The model measurements may then be output to feed to comparison step 308 according to the appropriate category.

Specifically, comparison step 308 may compare the measurements of the TIS subject received from step 304C of the QdMRI methodology to the categorized model measurements of the normal subjects received from the VGC in step 306E. This allows the system to determine the deviation of the TIS subject's thoraco-abdominal anatomy and dynamics from the age-group and gender-appropriate normal subject models of the thoraco-abdominal anatomy and dynamics. Further details of measurement comparison are found in the document beginning with "Specific Aims", filed concurrently herewith as Document5, and in Tong, et al. "Thoracic quantitative dynamic MRI to understand developmental changes in normal ventilatory dynamics", filed concurrently herewith as Document6, both which are incorporated by reference herein in their entireties.

QDMRI-VGC System Output

Figure 12:
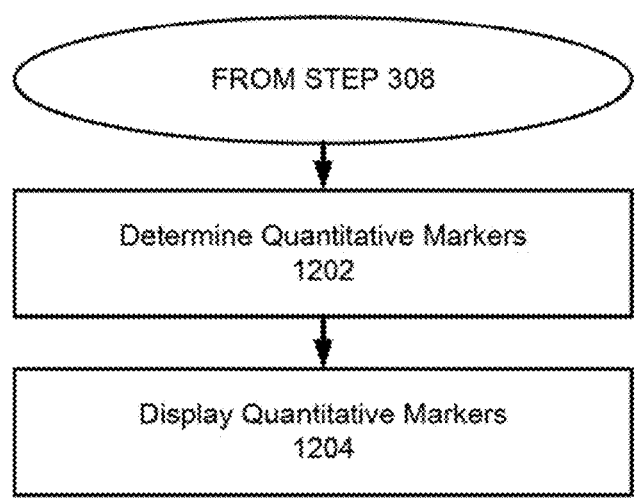
FIG. 12 is a flowchart of the quantitative marker step in the QdMRI-VGC flowchart, according to an aspect of the disclosure.

As described above, comparison step 308 determines the deviation from normal in the thoraco-abdominal anatomy and dynamics of the TIS subject. This information, as well as other information, may be output to the caregiver. For example, as shown in FIG. 12, various quantitative markers as a result of the comparison are determined in step 1202 and then displayed to the caregiver in step 1204. These quantitative markers may include (but are not limited to: individual left and right lung volumes at EI and EE; excursion tidal volumes of the left and right hemi-diaphragms and of the left and right chest wall; ratios of volumes or excursion tidal volumes of thoracic structures of interest; measurements of left-right asymmetry of volumes, excursion tidal volumes, or ratios for thoracic structures of interest; similarly architectural and tissual properties; growth properties; absolute and % deviations of one or more of these measurements or of composites of these measurements from those observed in the corresponding age-matched and gender-matched normal group.

Figure 13:
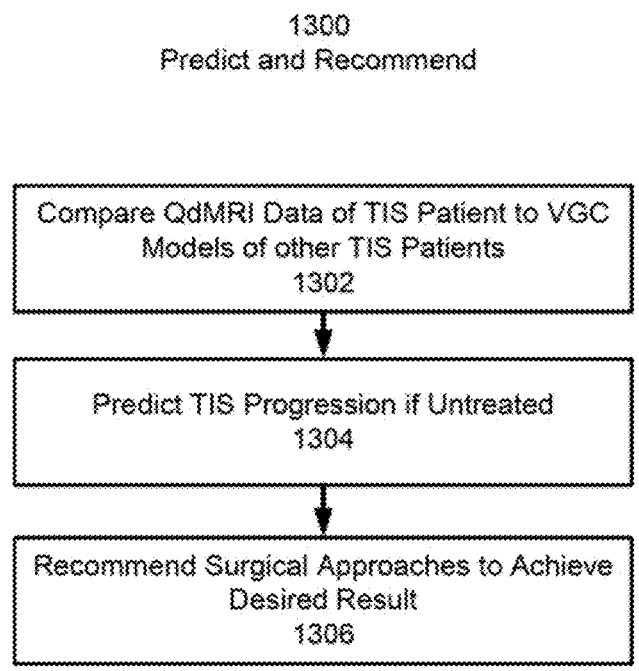
FIG. 13 is a flowchart of the TIS prediction/recommendation step in the QdMRI-VGC flowchart, according to an aspect of the disclosure.

In addition to outputting quantitative markers, the QdMRI-VGC system as shown in FIG. 13 may perform a prediction/recommendation step to address clinical or research questions of interest. This prediction/recommendation may include, but not limited to: a) determining if and when clinical decline of the TIS subject may occur during the process of aging, b) recommending when and how surgical procedures may be performed to best minimize the negative effects of the clinical disease progression for the TIS subject and to maximize patient outcomes, and c) providing evidence-based recommendations regarding the development of new surgical devices or new surgical procedures to optimally treat patients with TIS. For example, in step 1302, the system may compare the QdMRI data of the TIS subject to the VGC models of other TIS subjects (e.g. the VGC may store TIS anatomic models, TIS dynamic models and TIS growth models from QdMRI analyzed images of various TIS subjects). In step 1304, the system predicts the progression of TIS if left untreated. In step 1306, the system may also recommend surgical approaches to achieve a desired result over the growth of the child.

Other Applications

Although the QdMRI-VGC system has been described above as an application to TIS child subjects, the QdMRI-VGC system/method applies not just to children with TIS, but to any child or adult with a clinical condition that may potentially impact thoracic respiratory function even if subclinical (i.e., not symptomatic) in nature (e.g., early onset scoliosis, traumatic injury, presence of thoracic cancer, childhood asthma, etc.). In addition, the QdMRI-VGC system may be used for other anatomic applications such as the analysis of heart abnormalities (e.g. congenital heart defects) in subjects. Specifically, the QdMRI-VGC system may be utilized in children or adults with any condition that warrants evaluation with cardiac MRI (e.g., congenital heart disease before and after surgical repair, ischemic heart disease, cardiomyopathy, iatrogenic heart disease, etc.). Similar to lungs, a heart also has a volume and a cycle. The volume of the subject's abnormal heart and cardiac substructures may be measured and compared to models of normal subject hearts and cardiac substructures modeled over a cardiac cycle. Essentially, the QdMRI-VGC system may perform the same or similar steps to those shown in FIG. 3 for determining quantitative markers of an abnormal subject's heart deviation from normal.

Furthermore, the QdMRI-VGC system can be extended for use in adults. For example, patients with obstructive lung disease or restrictive lung disease, as well as patients who have undergone lung transplantation, may undergo QdMRI-VGC system evaluation to provide quantitative regional functional information about their respiratory mechanics that are otherwise not currently obtainable through computed tomography (CT), pulmonary function testing (PFT), or other methods of clinical assessment. The general principle of the QdMRI-VGC system is applicable even to non-dynamic structures throughout the body for assessing deviation from normality and monitoring changes as subject's age.

It is noted that the overall 4D image construction algorithm described above is applicable regardless of the application, and can be used to construct a 4D image of any anatomical feature (lungs, heart, muscles, etc.) of the subject that performs repetitive motion. In general, the three main 4D construction steps described above with respect to the TIS application may be modified to perform: 1) repetitive signal extraction for repetitive movement of any anatomical feature (i.e. repetitive signal extraction is achieved by performing optical flow estimation and deriving optical flux information), 2) cycle analysis of the repetitive movement of the anatomical feature (i.e. a full analysis of these repetitive cycles is conducted at each designated location based on the flux data to extract all near-normal cycles), and 3) 4D image formation for the anatomical feature (i.e. all near-normal cycles are aligned to one canonical repetitive movement model, one cycle for each designated location is proposed, and then the proposed cycles are then combined from all designated locations to form the final 4D image volume.).

CONCLUSION

The QdMRI-VGC steps described in FIGS. 3-13 may be performed by the computer 206, server 208 or a combination of both in FIG. 2A upon loading and executing software code or instructions which are tangibly stored on a tangible computer readable medium 226, such as on a magnetic medium, e.g., a computer hard drive, an optical medium, e.g., an optical disc, solid-state memory, e.g., flash memory, or other storage media known in the art. In one example, data are encrypted when written to memory, which is beneficial for use in any setting where privacy concerns such as protected health information is concerned. Any of the functionality performed by the computer described herein, such as the steps in FIGS. 3-13, may be implemented in software code or instructions which are tangibly stored on a tangible computer readable medium. Upon loading and executing such software code or instructions by the computer, the controller may perform any of the functionality of the computer described herein, including the steps in FIGS. 3-13 described herein.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises or includes a list of elements or steps does not include only those elements or steps but may include other elements or steps not expressly listed or inherent to such process, method, article, or apparatus. An element preceded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. Such amounts are intended to have a reasonable range that is consistent with the functions to which they relate and with what is customary in the art to which they pertain. For example, unless expressly stated otherwise, a parameter value or the like may vary by as much as ±10% from the stated amount.

In addition, in the foregoing Detailed Description, it can be seen that various features are grouped together in various examples for the purpose of streamlining the disclosure. This method of disclosure is not to be interpreted as reflecting an intention that the claimed examples require more features than are expressly recited in each claim. Rather, as the following claims reflect, the subject matter to be protected lies in less than all features of any single disclosed example. Thus, the following claims are hereby incorporated into the Detailed Description, with each claim standing on its own as a separately claimed subject matter.

While the foregoing has described what are considered to be the best mode and other examples, it is understood that various modifications may be made therein and that the subject matter disclosed herein may be implemented in various forms and examples, and that they may be applied in numerous applications, only some of which have been described herein. It is intended by the following claims to claim any and all modifications and variations that fall within the true scope of the present concepts.

The invention claimed is:

1. A method of analyzing thoracic insufficiency syndrome (TIS) in a subject, the method comprising the steps of:
    performing, by a processor, quantitative dynamic magnetic resonance imaging (QdMRI) analysis by:
        performing, by a processor, four-dimensional (4D) image construction of a TIS subject's thoracic cavity, the 4D image includes a sequence of two dimensional (2D) images of the TIS subject's thoracic cavity over a respiratory cycle of the TIS subject,
        segmenting, by the processor, a region of interest (ROI) within the 4D image,
        determining, by the processor, TIS measurements within the ROI,
        comparing, by the processor, the TIS measurements to normal measurements determined from ROIs in 4D images of the thoracic cavities of normal subjects that are not afflicted by TIS, and
        outputting, by the processor, quantitative markers indicating deviation of the thoracic cavity of the TIS subject relative to the thoracic cavities of the normal subjects.

2. The method of analyzing thoracic insufficiency syndrome (TIS) in a subject according to claim 1, further comprising the steps of:
    performing, by the processor, the 4D reconstruction by:
        estimating a motion vector field within the thoracic cavity from successive 2D images over a time period and, based on the motion vector field, outputting the respiratory cycles,
        filtering out abnormal respiratory cycles from the respiratory cycles, and
        assembling canonical cycles from the respiratory cycles and assembling the canonical cycles into the 4D image.

3. The method of analyzing thoracic insufficiency syndrome (TIS) in a subject according to claim 2, further comprising the steps of:
    estimating, by the processor, the motion vector field by estimating optical flow which assigns a vector to each pixel indicting movement of a portion of the thoracic cavity, and
    determining, by the processor, flux of the motion vector field indicating volume of the thoracic cavity during the respiratory cycle.

4. The method of analyzing thoracic insufficiency syndrome (TIS) in a subject according to claim 2, further comprising the steps of:
    identifying, by the processor, the respiratory cycles by identifying end-inspiration (EI) time points and end-expiration (EE) time points and then filtering out the respiratory cycles that deviate beyond a threshold.

5. The method of analyzing thoracic insufficiency syndrome (TIS) in a subject according to claim 2, further comprising the steps of:
    aligning, by the processor, the canonical cycles to one canonical respiration model,
    setting, by the processor, one cycle for each sagittal location independently, and
    combining, by the processor, the sagittal locations to form a final 4D image volume.

6. The method of analyzing thoracic insufficiency syndrome (TIS) in a subject according to claim 1,
    wherein the quantitative markers that are output by the processor include at least one of: individual left and right lung volumes at EI and EE, excursion tidal volumes of the left and right hemi-diaphragms and of the left and right chest wall, ratios of volumes or excursion tidal volumes of thoracic structures of interest, measurements of left-right asymmetry of volumes, excursion tidal volumes, or ratios for thoracic structures of interest; similarly architectural and tissual properties, growth properties, and absolute and percent deviations of one or more of these measurements or of composites of these measurements from those observed in the corresponding age-matched and gender-matched normal group.

7. The method of analyzing thoracic insufficiency syndrome (TIS) in a subject according to claim 1, further comprising the steps of:
    segmenting, by the processor, the ROI within the 4D image by:
        training a deep learning network with dMRI image slices and true segmentations of the lungs,
        specifying the ROI around the lung region in the 2D image representing a sagittal slice passing through the middle of the ipsilateral hemi-diaphragm, and propagating the ROI to all other 2D images, and
        segmenting all the 2D images within the ROI.

8. The method of analyzing thoracic insufficiency syndrome (TIS) in a subject according to claim 1,
    wherein the measurements include at least one of: left and right lung volume at end-inspiration, left and right lung volume at end-expiration, left and right chest wall tidal volumes, left and right hemi-diaphragm tidal volumes, left and right lung tidal volumes and total lung tidal volume.

9. The method of analyzing thoracic insufficiency syndrome (TIS) in a subject according to claim 1, further comprising the steps of:
    comparing, by the processor, the TIS measurements to normal measurements by determining a distance between a parameter vector of the TIS measurements and a distribution of the parameter vectors of the normal measurements.

10. The method of analyzing thoracic insufficiency syndrome (TIS) in a subject according to claim 9,
wherein the normal measurements are determined from an average thoracic cavity of the normal subjects, an average respiratory cycle of the thoracic cavity of the normal subjects, and a growth of the thoracic cavity of the normal subjects over time.

11. A method for creating a virtual growing child (VGC) database of anatomic models for use in analyzing thoracic insufficiency syndrome (TIS) in a subject, the method comprising the steps of:
creating, by a processor, VGC database of anatomic models by:
performing, by a processor, four-dimensional (4D) image constructions of the thoracic cavities of normal subjects that are not afflicted by TIS, the 4D images each include a sequence of two dimensional (2D) images of the normal subject's thoracic cavity over a respiratory cycle of the normal subject,
segmenting, by the processor, a region of interest (ROI) within each of the 4D images,
determining, by the processor, normal measurements within each of ROI,
generating, by the processor, based on the normal measurements, a group-wise anatomic model representing an average thoracic cavity of the normal subjects,
generating, by the processor, based on the normal measurements, a group-wise dynamic model representing an average respiratory cycle of the thoracic cavity of the normal subjects,
generating, by the processor, based on the normal measurements, a growth model representing growth of the thoracic cavity of the normal subjects over time,
categorizing, by the processor, measurements from the group-wise anatomic model, the group-wise dynamic model and the growth model, and
outputting the categorized measurements for comparison to TIS measurements of a TIS subject.

12. The method for creating a virtual growing child (VGC) database of anatomic models for use in analyzing thoracic insufficiency syndrome (TIS) in a subject according to claim 11,
wherein the group-wise anatomic model includes the average volumetric dimensions of the average thoracic cavity of the normal subjects at a given phase in the respiratory cycle.

13. The method for creating a virtual growing child (VGC) database of anatomic models for use in analyzing thoracic insufficiency syndrome (TIS) in a subject according to claim 11,
wherein the group-wise dynamic model includes an ensemble of group-wise anatomic models determined at a plurality of given phases in the respiratory cycle.

14. The method for creating a virtual growing child (VGC) database of anatomic models for use in analyzing thoracic insufficiency syndrome (TIS) in a subject according to claim 11,
wherein the growth model includes a male growth model and a female growth model.

15. The method for creating a virtual growing child (VGC) database of anatomic models for use in analyzing thoracic insufficiency syndrome (TIS) in a subject according to claim 11,
wherein the growth model includes group-wise dynamic models for each of a plurality of ages.

16. The method for creating virtual growing child (VGC) database of anatomic models for use in analyzing thoracic insufficiency syndrome (TIS) in a subject according to claim 11,
wherein the processor categorizes the measurements from the group-wise anatomic model, the group-wise dynamic model and the growth model by age groups.

17. The method for creating a virtual growing child (VGC) database of anatomic models for use in analyzing thoracic insufficiency syndrome (TIS) in a subject according to claim 11,
wherein the processor categorizes the measurements from the group-wise anatomic model, the group-wise dynamic model and the growth model into at least one of a morphological category, an architectural category, a tissual category, a dynamic category, and developmental category.

18. The method for creating a virtual growing child (VGC) database of anatomic models for use in analyzing thoracic insufficiency syndrome (TIS) in a subject according to claim 17,
wherein the morphological category includes at least one of shape, size and geometrical properties of structures in the thoracic cavity at each time point in the respiratory cycle,
wherein the architectural category includes at least one of geographical layout of the structures in the thoracic cavity and their inter-relationships at each time point in the respiratory cycle,
wherein the tissual category includes at least one of properties of soft tissues and lung parenchyma at each time point in the respiratory cycle,
wherein the dynamic category includes at least one of a change in morphological, architectural and tissual properties over time in the respiratory cycle, and
wherein the developmental category includes at least a change in the dynamic properties with growth.

19. A method for analyzing heart abnormalities in as subject, the method comprising the steps of:
performing, by a processor, quantitative dynamic magnetic resonance imaging (QdMRI) analysis by:
performing, by a processor, four-dimensional (4D) image construction of a subject's heart, the 4D image includes a sequence of two dimensional (2D) images of the subject's heart over a cardiac cycle of the subject,
segmenting, by the processor, a region of interest (ROI) within the 4D image,
determining, by the processor, heart measurements within the ROI,
comparing, by the processor, the heart measurements to normal measurements determined from ROIs in 4D images of the heart of normal subjects that are not afflicted by heart abnormalities, and
outputting, by the processor, quantitative markers indicating deviation of the heart of the subject relative to the heart of the normal subjects.

20. A method for creating a virtual growing child (VGC) database of anatomic models for use in analyzing heart abnormalities in a subject, the method comprising the steps of:
performing, by a processor, VGC analysis by:
performing, by a processor, four-dimensional (4D) image constructions of the hearts of normal subjects that are not afflicted by heart abnormalities, the 4D images each include a sequence of 2D dimensional (2D) images of the normal subject's heart over a cardiac cycle of the normal subject, segmenting, by the processor, a region of interest (ROI) within each of the 4D images, determining, by the processor, normal measurements within each of ROI, generating, by the processor, based on the normal measurements, a group-wise anatomic model representing an average heart of the normal subjects, generating, by the processor, based on the normal measurements, a group-wise dynamic model representing an average heart of the normal subjects, generating, by the processor, based on the normal measurements, a growth model representing growth of the heart of the normal subjects over time, categorizing, by the processor, measurements from the group-wise anatomic model, the group-wise dynamic model and the growth model, and outputting the categorized measurements for comparison to heart measurements of a heart subject with heart abnormalities.

21. A method of analyzing a clinical condition that affects a thoracic respiratory function in an afflicted subject, the method comprising the steps of:

performing, by a processor, quantitative dynamic magnetic resonance imaging (QdMRI) analysis by:

performing, by a processor, four-dimensional (4D) image construction of the afflicted subject's thoracic cavity, the 4D image includes a sequence of two dimensional (2D) images of the afflicted subject's thoracic cavity over a respiratory cycle of the afflicted subject, segmenting, by the processor, a region of interest (ROI) within the 4D image, determining, by the processor, afflicted measurements within the ROI, comparing, by the processor, the afflicted measurements to normal measurements determined from ROIs in 4D images of the thoracic cavities of normal subjects that are not afflicted, and outputting, by the processor, quantitative markers indicating thoracic respiratory function deviation of the afflicted subject relative to the respiratory function of the normal subjects.

22. A method of performing four-dimensional (4D) image construction of an anatomical feature of a subject, the method comprising the steps of:

estimating, by a processor, a motion vector field for the anatomical feature from successive two-dimensional (2D) images over a time period, and, based on the motion vector field, outputting repetitive cycles;

filtering out, by the processor, abnormal cycles from the repetitive cycles; and assembling, by the processor, canonical cycles from the filtered repetitive cycles and assembling the canonical cycles into the 4D image.

23. The method of performing four-dimensional (4D) image construction of an anatomical feature of a subject according to claim 22, further comprising the steps of:

aligning, by the processor, the canonical cycles to one canonical repetitive model;

setting, by the processor, one cycle for each of a plurality of designated locations on the anatomical feature independently; and combining, by the processor, the designated locations to form a final 4D image volume.

* * * * *